United States Patent [19]

Caciagli et al.

[11] Patent Number: 4,810,779
[45] Date of Patent: Mar. 7, 1989

[54] DECAPEPTIDES HAVING HYPOTENSIVE ACTION AND PROCESS FOR THEIR PREPARATION

[75] Inventors: Valerio Caciagli, Rome; Antonio S. Verdini, Monterotondo; Giovanna De Luca, Rome; Giovanni Di Stazio, Rome; Vincenzo Politi, Rome, all of Italy

[73] Assignee: Enichem Elastomeri S.p.A., Palermo, Italy

[21] Appl. No.: 870,161

[22] Filed: Jun. 3, 1986

[30] Foreign Application Priority Data

Jun. 5, 1985 [IT] Italy .................. 21041 A/85

[51] Int. Cl.$^4$ .................. C07K 7/06; A61K 37/02
[52] U.S. Cl. .................. 530/328; 530/334; 530/800; 548/344
[58] Field of Search .......... 530/328, 314, 316, 334, 530/800, 315, 330; 514/15

[56] References Cited

U.S. PATENT DOCUMENTS

| | | | |
|---|---|---|---|
| 3,546,198 | 12/1970 | Mazur | 530/314 |
| 3,562,244 | 2/1971 | Bodansky et al. | 530/315 |
| 3,832,337 | 8/1974 | Ondetti et al. | 530/328 |
| 4,108,846 | 8/1978 | Meienhofer et al. | 530/334 |
| 4,591,648 | 5/1986 | Jones et al. | 548/344 |
| 4,658,016 | 4/1987 | Konig et al. | 530/330 |

FOREIGN PATENT DOCUMENTS 49727 12/1982 Italy .

OTHER PUBLICATIONS

Peptide Synthesis, pp. 323–338, 355–363.
Pettit R. G., Synthetic Peptides, vol. 1, 1970, p. 5.
The Proteins, vol. II, Neurath et al., 322–323, 3rd ed., 1976.

*Primary Examiner*—Delbert R. Phillips
*Assistant Examiner*—T. D. Wessendorf
*Attorney, Agent, or Firm*—Hedman, Gibson, Costigan & Hoare

[57] ABSTRACT

New decapeptides having hypotensive action are disclosed, which can be defined by the formula:

GLp-Leu-Trp-Pro-X-Pro-Y-Z-Pro-Pro-OH    (I)

wherein:
X=Arg or Orn
Y=His or Gln
Z=Ile or Val with the following limitations:
when
  X=Arg:
  Y=His
  Z=Val;
when
  X=Orn:
  Y=Gln
  Z=Ile;
or, when
  X=Orn:
  Y=His
  Z=Val and pharmaceutically acceptable salts, amides of alkyl esters thereof.

9 Claims, No Drawings

DECAPEPTIDES HAVING HYPOTENSIVE ACTION AND PROCESS FOR THEIR PREPARATION

The present invention relates to novel decapeptides having hypotensive action, useful for the management of hypertension states.

From the technical and patent literature, numerous peptides are known, containing a number of aminoacidic residues ranging from 5 to 13, extracted from snake poison, capable of causing a reduction in arterial pressure in mammals.

Among the peptides extracted from the venom of snake Bothrops Jararaca, the nonapeptide $BPP_{9a}$, known as Teprotide, has resulted in a powerful antihypertensive agent.

However, said compounds performs its action only when it is administered by intravenous way, and is inactive when administered orally.

Italian Patent Application No. 49727 A/82 of Dec. 22, 1982, discloses a new decapeptide having hypotensive action, isolated from the venom of snake Crotalus Atrox corresponding to the structure:

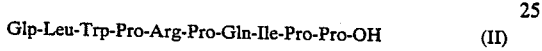

Glp-Leu-Trp-Pro-Arg-Pro-Gln-Ile-Pro-Pro-OH    (II)

Said decapeptide, injected into the femoral vein of rats, causes a lowering in arterial pressure and potentiates the activity of bradykinin, prolonging the hypotensive effect thereof.

A high-yield synthesis of decapeptides of formula II presents however difficulties, which render the same process unfavourable from the economic viewpoint, or anyway not much suitable to a large-scale application.

The reasons for such drawbacks in the synthesis in solid phase are to be found mainly (a) in the formation of a cyclic compound, diketopiperazine [(Pro)$_2$ cycle], at the beginning of the third step of the assemblage of the peptide chain, and (b) in the use of arginine derivatives, for which the final acidolytic removal of the guaindine-moiety protecting group is unsatisfactory.

We have found now that, by replacing the arginine present in the 5-position of decapeptide II by ornithine, a decapeptide is obtained which, besides maintaining its biological activity, can be used as precursor for the preparation of the known decapeptide of formula (II).

We have furthermore replaced the dipeptide fragment Gln-Ile present in 7- and 8-positions of decapeptide (II) with the dipeptide fragment His-Val, obtaining analogous which, besides maintaining the hypotensive activity, display a more pronounced effect on the inhibition of the enzyme which converts Angiotensin I into Angiotensin II.

The said decapeptides are synthetized in solid phase on polymeric matrix, by using synthesis strategies which allow us to overcome the above reported drawbacks.

Accordingly, a purpose of the present invention are decapeptides having hypotensive action, which can be defined by the following general formula:

Glp-Leu-Trp-Pro-X-Pro-Y-Z-Pro-Pro-OH    (I)

wherein:
X=Arg or Orn
Y=His or Gln
Z=Ile or Val
with the following limitations:
when
   X=Arg:
   Y=His
   Z=Val;
when
   X=Orn:
   Y=Gln
   Z=Ile;
or, when
   X=Orn:
   Y=His
   Z=Val;
and pharmaceutically acceptable salts, amides of alkyl esters thereof.

In the foregoing formula (I), the terms have the following meaning:
Glp=Pyroglutamic acid
Leu=Leucine
Pro'Proline
Trp=Tryptophan
Arg=Arginine
His=Histidine
Val=Valine
Ile=Isoleucine
Orn=Ornithine
Gln=Glutamine A process of the present invention is furthermore a process for the preparation of decapeptides of formula (I) by the use of synthesis strategies comprising:

(a) the preliminary preparation of a dipeptide derivative Fmoc-Z-Pro-OH, wherein Z has the above reported meaning;

(b) the use of the derivative Fmoc-Orn(Boc)-OH in lieu of a derivative of arginine;

(c) the use of the derivative Fmoc-His(Trt)-OH for histidine.

In particular, the preparation of decapeptide of formula (I) wherein X=Orn, Y=Gln and Z=Ile, corresponding to the structure:

Glp-Leu-Trp-Pro-Orn-Pro-Gln-Ile-Pro-Pro-OH    (III)

comprises the preliminary preparation of the dipeptide derivative Fmoc-Ile-Pro-OH.

The preparation of the above-said derivative allows the formation of the diketopiperazine [(Pro)$_2$ cycle] to be avoided during the step of assemblage of the peptide chain.

Decapeptide (III) injected in the removal vein of male rats, causes a stronger and more long-lasting hypotensive effect than decapeptide (II) and shows a pressure differential of 25 $mm_{Hg}$ on minimum, and of 20 $mm_{Hg}$ on maximum pressure.

It furthermore potentiates the hypotensive effect of bradykinin, and shows an eurhythmizing effect.

Decapeptide (III) is a valuable precursor for the preparation of decapeptide of formula (II).

The introduction of the guanidyl moiety into decapeptide (III), by using O-methylisourea, according to the method as described by C. G. Granier et al. [Eur. J. Biochem. 82, 293 (1978)], allows us to obtain decapeptide (II) in a simple way and with yields higher than 70%.

According to the present invention, the preparation of decapeptide of formula (I), wherein X=Orn, Y=His and Z=Val, to be represented by the formula:

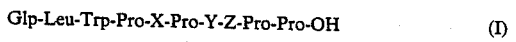

Glp-Leu-Trp-Pro-Orn-Pro-His-Val-Pro-Pro-OH    (IV)

comprises:

(a) the preliminary preparation of the dipeptide derivative Fmoc-Val-Pro-OH and (b) the use, for the assemblage of the peptide chain, of the peptide derivative Fmoc-His(Trt)-OH.

The preliminary preparation of derivative Fmoc-Val-Pro-OH allows avoiding cyclization problems in the assemblage step, as reported hereinabove.

According to the present invention, said dipeptide derivative is synthetized by condensing Fmoc-Val-O-PFP (pentafluorophenylester) with Pro-OH.

This synthesis strategy allows the presence to be avoided of such impurities as Fmoc-(Val-Pro)$_2$-OH and of the product of double acylation of peptide derivative Fmoc-Val-Pro-OH used in the decapeptide preparation, and hence the formation of peptide analogous containing supernumerary valine and proline residue.

The synthesis and the use of derivative Fmoc-His-(Trt)-OH in the step of assemblage of decapeptide (IV) allows the problem to be overcome, which arises from the contemporaneous presence of His and Trp residues in the decapeptide.

The benzyloxymethyl group is considered by those skilled in the art as the elective group for the protection of the imidazole moiety of histidine, both because it allows an efficacious protection during the synthesis of the decapeptide, and because it can be removed under mild conditions by catalytic hydrogenation.

However, the removal of said protector group by catalytic hydrogenation causes at the same time a considerable reduction of the indolic ring of tryptophan residue.

By the synthesis and the use of the peptide derivative fluorenylmethoxycarbonylhistidine-N$^{im}$trityl [Fmoc-His(Trt)-OH], obtaining has been possible the removal of the protecting group from the His residue during the acidolytic step, provided by the Sheppard's methodology [E. Atherton, J. Chem. Soc. Perkin I, 583 (1984)] for separating the peptide from its polymeric support, thus the reduction of tryptophan residue being avoided.

In this stage, the contemporaneous removal takes place furthermore of all the protecting groups of side chains, labile under acidic conditions. Decapeptide (IV), by guanidylation by O-isomethylurea, is transformed, with a yield of 70%, into the decapeptide having formula Glp-Leu-Trp-Pro-Arg-Pro-His-Val-Pro-Pro-OH    (V)

Both the decapeptide (IV) and decapeptide (V) cause in vivo a hypotensive effect, and potentiate the activity of bradykinin.

According to the present invention, decapeptides (I) are synthetized, according to known techniques, in solid phase or polymeric matrix of polyamidic type.

The resin, activated with 1,2-diamino-ethane, according to the methodology as described by Sheppard et al. [E. Atherton, J. Chem. Soc. Perkin I, 583 (1981)], is modified by treatment with the symmetrical anhydride of fluorenylmethyloxycarbonylnorleucine (Fmoc Nle)$_2$O and, after removal of Fmoc with piperidine at 20% in dimethylformamide (DMF), is acylated with 2,4,5-trichlorophenyl p-hydroxymethylphenoxyacetate.

To the resin so modified the first aminoacid is bound, by an ester bond, activated separately and under suitable conditions, as its symmetrical anhydride.

The subsequent aminoacids are introduced sequentially in the polymer according to the desired order, and the completion of formation of amidic bond is verified according to the E. Kaiser' method [Anal. Biochem. 34 (1970), 595].

At the end of the synthesis, the decapeptide is separated from th resin, and is purified by High Pressure Liquid Chromatography. Typically, such a process is carried out by using a Jobin-Yvon ® chromatograph Model Miniprep, with Lichroprep ® RP-18 (20–40µ) packing and eluting with an aqueous mixture containing 0.1% of trifluoroacetic acid, and $CH_3CN$ at 28% by volume.

The functional groups present in aminoacids are protected by using temporary protecting groups selected among those known in the synthesis of peptides and compatible with the synthesis strategies adopted.

The identity of synthetized products has been checked by protonic nuclear magnetic resonance spectroscopic analysis ($^1$H-N.M.R.).

The purity of decapeptides is also verified by Reverse-Phase High Pressure Liquid Chromatography (RP-HPLC), using a column with Bondapek ® C-18, 10 µm packing, eluting with an aqueous phase containing 0.1% of trifluoroacetic acid (TFA) and $CH_3CN$ at 34–36% by volume.

The analysis of the aminoacids has been carried out by hydrolysis with 6N hydrochloric acid or 3N methanesulphonic acids inside sealed ampuls, at 120° C. and for a time of 18 hours.

The decapeptides of the present invention form salts, amides, or alkyl esters, which too are within the scope of the present invention.

Preferably, non-toxic salts, acceptable from the physiological viewpoint, are prepared, such as, e.g., potassium or sodium salts, and salts of aminoacids.

These, and the other non-physiologically-acceptable salts can be used, for example, in the isolation and purification of the decapeptides of the present invention.

Hypertension can be alleviated in all mammalian species, including man, by the administration of a composition containing a therapeutically effective amount of a decapeptide of formula (I) and a pharmaceutically acceptable support.

The activity of the decapeptides of the present invention has been determined in vivo on C.D. male rats available from Charles-River Co., anesthetized by ethyl urethane.

The effect on the arterial pressure and on bradykinin potentating has been studied by injecting into femoral vein a decapeptide (I) in an amount of from 0.3 to 0.2 mg/kg of body weight.

The following experimental Examples are illustrative and not limitative of the invention.

EXAMPLE 1

Synthesis of Fluorenylmethoxycarbonylisoleucylproline (Fmoc-Ile-Pro-OH)

An amount of 3.27 g (10 mol) of Boc-Ile-Pro-OH, prepared according to the method as disclosed in E. W. B. De Leer et al [Rec. Trav. Chim. Pays Bas, 92 (1973), 174], is reacted with 20 ml of a mixture of $CH_2Cl_2$/trifluoroacetic acid (TFA) (1:1, v/v) at room temperature (20°–25° C.) for 30 minutes.

At the end of such time period, the solvent is evaporated to dryness, the residue is redissolved with 50 ml of a methanol/ethyl ether (1:2, v/v) mixture, and the residue is precipitated again by adding 20 ml of ethyl ether (Et$_2$O), while keeping the mixture at room temperature for 3 hours under stirring, and overnight (about 12 hours) without stirring.

The precipitate is then filtered off under nitrogen stream.

2.6 g of product with melting point (M.P.) 151°–152° C. is obtained.

The product so obtained is dissolved in a mixture constituted by 25 ml of Na$_2$CO$_3$ at 10% and 20 ml of dioxane.

To said mixture, kept stirred and at 0° C., 1.5 g of fluorenylmethylchloroformate dissolved in 9 ml of dioxane is added dropwise over a time of about 10 minutes.

The mixture is reacted at 0° C. for 2 hours and at 15° C. for 1 hour.

The mixture is then added to 50 ml of H$_2$O, is washed three times, each time with 50 ml of Et$_2$O, is made acid to pH 3 by 0.1N HCl, and is extracted three times, each time with 100 ml of Et$_2$O.

The organic extracts, after separation, are combined, dried over MgSO$_4$, filtered and brought again to dryness.

2.7 g is thus obtained of product Fmoc-Ile-Pro-OH (yield 60%), with:

$[\alpha]_{25}\cdot^{589} = 73.2°$ c=1.5 in dimethylformamide (DMF)

On $^1$H-N.M.R. analysis [(CD$_3$)SO] δ 0.70–2.20 (13H, λCH$_3$Ile, δCH$_3$Ile, λCH$_2$Ile, βCHIle, βCH$_2$Pro, λCH$_2$Pro), 3,55 (2H, δCH$_2$Pro), 3.85–4.50 (5H, αCH-Pro, αCHIle, CH$_2$Fmoc, CHFmoc), 7.10–8.00 (9H, CONH φ).

EXAMPLE 2

Synthesis of
Glp-Leu-Trp-Pro-Orn-Pro-Gln-Ile-Pro-Pro-OH (III)

0.5 g of polymeric support, constituted by small spheres of polydimethylacrylamide-co-acryloylsarcosyne methylester crosslinked with N,N'-ethylene-bis-acrylamide, is activated with 1,2-diaminoethane.

The resin so activated is reacted with 0.620 g (0.9 mmol) of (FmocNLe)$_2$O and then, after removal of Fmoc by piperidine at 20% in DMF, is acylated with 0.325 g (0.9 mmol) of 2,4,5-trichlorophenol p-hydroxymethylphenoxyacetate.

The resin so modified contains eventually 0.55 mmol/g of norleucine.

The ester bond with the first aminoacid is realized by treating the modified resin at 20°–25° C. for 30 minutes with 0.591 g (0.9 mmol) of (FmocPro)$_2$O dissolved in 8 ml of DMF, in the presence of 0.9 mmol of N-methyl-morpholine and 0.0109 g (0.09 mmol) of 4-dimethylaminopyridine.

The subsequent aminoacids are sequentially introduced into the polymer in the order as reported in Table 1, by following the general procedures and one of the acylation procedure as described in Table 2.

The decapeptide reaction synthesis is carried out using a Beckman ® Model 990B automatic synthetizer, by means of one of the acylation procedures disclosed in Table 2.

The symmetrical anhydrides are preformed at the acylation time by operating as follows.

1.8 mmol of aminoacids derivative is reacted with 0.185 g (0.9 mmol) of N,N'-dicyclohexylcarbodiimide in 20 ml of CH$_2$Cl$_2$, at room temperature for 10 minutes, the dicyclohexylurea formed is filtered off, and CH$_2$Cl$_2$ is evaporated.

The symmetrical anhydride so obtained is then dissolved in 8 ml of DMF and used for the acylation.

For each acylation, the completion of the amidic bond formation is verified by reacting a sample of resin with ninhydrin according to Kaiser's method [E. Kaiser, Anal. Biochem, 34 (1970), 595].

After the addition of the last aminoacid, the resin is suspended in 20 ml of a solution at 10% (v/v) of ethanedithiol in trifluoroacetic acid for 2 hours.

The resin is then separated from the reaction mixture, by filtration under nitrogen, the resin is washed with 20 ml of H$_2$O for three times, and is filtered. The combined filtrates are extracted four times, each time with 50 ml of Et$_2$O.

The aqueous phase is then evaporated off and 240 μmol of raw peptide (III) is recovered.

The peptide so obtained in dissolved in water and fractions, each containing 10 μmol of peptide, are chromatographed by High Pressure Liquid Chromatography, using a Jobin-Yvon ® Model Miniprep chromatograph with Lichroprep ® RP-18 20–40 μm (Merck) packing, and eluting with a mixture of 72% of H$_2$O, 28% of CH$_3$CN, and containing 0.1% of TFA.

For each chromatographic run, evaporated and freeze-dried, 6.6 μmol of peptide is isolated.

Analysis of Aminoacids by Hydrolysis with 6N HCl: 2Glu 2.10; 4Pro 4.06; 1Ile 0.94; 1Orn 1.003; 1Leu 1.00.

Analysis of Aminoacids by Hydrolysis with 3N Methanesulphonic acid: 2Glu 2.10; 4Pro 3.80; 1Ile 1.01; 1Orn 1.06; 1Trp 0.93; 1Leu 1.00.

The purity of peptide is verified by High Pressure Liquid Chromatography, by using a 10-cm long column of 0.5 cm in diameter, with Bondapek ® C-18, 10 μm (E. Merck Co., Darmstadt) packing, and carrying out the elution by an aqueous phase containing 0.1% of TFA and 34% by volume of CH$_3$CN.

EXAMPLE 3

Synthesis of
Glp-Leu-Trp-Pro-Arg-Pro-Gln-Ile-Pro-Pro-OH 5.94 μmol of compound (III), obtained as reported in Example 2, is dissolved in 5 ml of 0.5M O-methylisourea and brought to pH 10 with 0.05N NaOH.

The solution is kept at room temperature for 20 hours.

At the end of said time period, the solution in concentrated in vacuo up to 2.5 ml, is made acid to pH 3.5 with TFA and is finally desalted by High Pressure Liquid Chromatography, using a Jobin-Yvon ® Model Miniprep chromatograph with a packing of Lichroprep ® RP-18 20–40 μm resin (Merck) and as the eluant phase, an H$_2$O-CH$_3$CN-TFA (75:25:0.1) mixture.

The chromatographed fractions corresponding to the peptide, evaporated and freeze-dried, allow 4.32 μmol of peptide (II) to be isolated, with a yield of 72.7%.

Analysis of Aminoacids by Hydrolysis with 6N HCl: 2Glu 2.10; 4Pro 3.78; 1Ile 0.91; 1Arg 0.99; 1Leu 1.00.

Analysis of Aminoacids by Hydrolysis with 3N Methanesulphonic acid: 2Glu 2.10; 4Pro 3.85; 1Ile 0.99; 1Arg 0.93; 1Trp 0.92; 1Leu 1.00.

The purity of peptide is verified according to as disclosed in Example 2.

EXAMPLE 4

Synthesis of Fluorenylmethoxycarbonylvalylproline (Fmoc-Val-Pro-OH)

3.418 g (7 mmol) of fluorenylmethoxycarbonylvalylproline pentafluorophenyl ester prepared according to the method as disclosed by L. Kisfaduly et al. [Synthesis, 325 (1983)] is dissolved in 10 ml of DMF containing 0.805 g (7 mmol) of proline and 1.9 ml of triethylamine.

The resulting mixture is kept at 20°–25° C., under stirring, for 10 minutes.

The solvent is evaporated to dryness, and the residue is dissolved in 50 ml of chloroform.

Said mixture is then washed three times, each time with 50 ml of 1H HCl and two times, each time with 10 ml of $H_2O$.

The organic extracts are combined, dried over $MgSO_4$, filtered and from them the solvent is finally evaporated to dryness on Rotavapor Model Büchi EL130.

4.7 g of raw product is thus obtained.

Said product is dissolved in 20 ml of a mixture of ethyl acetate/ethyl ether (EtOAc/$Et_2O$) (1:3, v/v), brought to incipient precipitation with 50 ml of hexane and then maintained at 4° C. for 2 hours. By decantation, 0.5 g of precipitate is separated which, on T.L.C. analysis, results constituted by two products.

To the mother liquor, 250 ml of hexane is added dropwise over a time of about 5 minutes; from the resulting mass, after filtration 2.8 g of solid white precipitate is obtained (yield 64.1%) with $[\alpha]_{25}°^{589} = 58.2°$ (c=1.5 in DMF).

At $^1$H-N.M.R. analysis (CDCl$_3$): $\delta$1.95 (d. 6H, CH$_3$Val), 1.50–2.35 (5H, $\beta$CH$_2$Pro, $\lambda$CH$_2$Pro, $\beta$CHVal), 3,63 (m. 2H, $\delta$CH$_2$Pro), 3.90–4.50 (5.17, CHFmoc, CH$_2$Fmoc, $\alpha$CHVal, $\alpha$CHPro), 7.10–8.0 (9H, $\phi$, CONH), 12.00 (broad S. 1H, COOH).

EXAMPLE 5

Synthesis of
Fluorenylmethoxycarbonylhistidine-N$^{im}$triethyl (Fmoc-His(Trt)-OH)

2.461 g (6.2 mmol) of N$^{im}$-(Trt)His-OH, obtained according to as reported by G. C. Stelakatos et al. [J. Am. Chem. Soc. 81, 2884 (1959) and Von Gunter Fosse and V. Krychwski, I. Prakt. Chem., B 312, 1097 (1970)], is dissolved in a mixture constituted by 30 ml of Na$_2$CO$_3$ at 10% and 25 ml of dioxane. To said solution, 2.1 g (8.1 mmol) of fluorenylmethylchloroformate in 20 ml of dioxane is then added.

The reaction mixture is then kept at 0° C. for 1 hour and at room temperature for 2 hours.

The solvent is evaporated to dryness and the residue is redissolved with 200 ml of $H_2O$.

The aqueous solution is washed three times, each time with 20 ml of $Et_2O$, made acid to pH 6, and extracted three times, each time with 100 ml of EtOAc.

The separated organic extracts are combined and dried over $MgSO_4$, filtered and concentrated to dryness under vacuum.

3.45 g of spongy solid is thus obtained (yield 88.9%), with M.P.=185°–188° C.

Said product is purified by crystallization with an EtOAc/$Et_2O$ (1:4, v/v) mixture, 2.45 g being obtained of pure product with $[\alpha]_{25}°^{589}$=+1.5° (c=1.5, absolute ethanol) and M.P.=192°–197° C.

$^1$H-N.M.R. analysis (CD$_3$SO) $\delta$2.92 (m. 2H, $\beta$CH$_2$His), 3.85–4.50 (4H, CH$_2$Fmoc, CHFmoc, $\alpha$CH-His), 6.75–8.00 (24H, CHHis, CONH, $\phi$).

EXAMPLE 6

Synthesis of
Glp-Leu-Trp-Pro-Orn-Pro-His-Val-Pro-Pro-OH (IV)

The process is carried out as in Example 2, at the end a modified resin containing 0.81 mmol/g of norleucine being obtained.

The aminoacids are introduced sequentially on the polymer according to the order as reported in Table 3, by following the acylation procedures as described in Table 2.

220 $\mu$mol is obtained of raw peptide which, submitted to High Pressure Liquid Chromatography as reported in Example 2, yields, for each run, evaporated and freeze-dried, 7.2 $\mu$mol of peptide.

Analysis of Aminoacids by Hydrolysis with 6N HCl: 1Glu 1.10; 4Pro 4.21; 1Val 1.05; 1His and 1Orn (not determined); 1Leu 1.

Analysis of Aminoacids by Hydrolysis with 3N Methanesulphonic acid: 1Glu 1.10; 4Pro 4.18; 1Val 1.06; 1His and 1Orn (not determined); 1Trp 0.94; 1Leu 1.

The purity of peptide is verified according to as reported in Example 2.

EXAMPLE 7

Synthesis of
Glp-Leu-Trp-Pro-Arg-Pro-His-Val-Pro-Pro-OH (V)

The synthesis is carried out as described in Example 3, using 4.2 $\mu$mol of compound (IV) obtained as reported in Example 6.

The chromatographic fractions corresponding to the peptide, evaporated and freeze-dried, allow 2.98 $\mu$mol of peptide (71%) to be isolated.

Analysis of Aminoacids by Hydrolysis with 6N HCl: 1Glu 1.05; 4Pro 3.97; 1Val 0.93; 1His 1.04; 1Arg 0.97; 1Leu 1.

Analysis of Aminoacids by Hydrolysis with 3N Methanesulphonic acid: 1Glu 1.06; 4Pro 4.09; 1Val 0.99; 1His 1.0; 1Arg 0.95; 1Trp 0.93; 1Leu 1.

Purity of peptide is confirmed by liquid chromatography, as previously reported, but modifying the eluant phase with CH$_3$CN at 46% by volume.

EXAMPLE 8

Effect of the Decapeptides on Arterial Pressure

Five C.D. male rats available from Charles River Co., of weight of 200–300 g, anaesthetized by ethyl urethane (1.75 g/kg by intraperitoneal way) are used.

After tracheal cannulating, the right-hand carotid artery is isolated and connected by cannula to a Hewlett-Packard Model 1280 pressure transducer.

From isolated left-hand carotid the arterial flow is recorded by means of Biotronex ® electromagnetic flowmeter, and pressure variation wiith the (dp/dt), electrocardiogram (ECG) and the beats per minute (BPM) are recorded on Hewlett Packard Polygraph.

The decapeptides of the present invention have been tested by being injected into right-hand femoral vein at the dose of 0.3–0.2 mg/kg of body weight, and compared to the decapeptide (II) of the prior art.

The results of the hypotensive effect and its duration are reported in Table 4.

As it can be observed from Table 4, decapeptide (III) causes a stronger and more long-lasting hypotensive effect than decapeptide (II) of the prior art.

EXAMPLE 9

Effect of Decapeptides as Bradykinin Potentiators

Male C.D. rats of Charles-River race are treated as described in Example 8, and submitted to test by bradykinin.

Bradykinin is a physiologic peptide which, when injected into femoral vein, causes a fast but not long-lasting hypotensive effect, because it is rapidly degraded at pulmonary circulation level by the Angiotensin Conversion Enzyme (ACE).

The peptides of the present invention are tested by being injected into the right-hand femoral vein soon before bradykinin, and comparing them to the decapeptide of the prior art.

The results of bradykinin-potentiating effect and it duration are reported in Table 5.

TABLE 1

ORDER OF ADDITION OF THE AMINOACIDIC AND PEPTIDE DERIVATIVES USED IN THE SYNTHESIS AND PROCEDURE USED

| Derivative | Procedure |
| --- | --- |
| 1 Fmoc Ile—Pro | 4b |
| 2 Fmoc—Gln | 4c |
| 3 Fmoc Pro | 4a |
| 4 $N^\alpha$—Fmoc, $N^\delta$—Boc Orn | 4a |
| 5 Fmoc Pro | 4a |
| 6 Fmoc Trp | 4a |
| 7 Fmoc Leu | 4a |
| 8 Fmoc Glp | 4d |

TABLE 2

PROCEDURES FOR THE SYNTHESIS IN SOLID PHASE ON POLYAMIDIC MATRICES

| | |
| --- | --- |
| 1  5 Washings with DMF | |
| 2  Treatments with piperidine at 20% in DMF | |
| 3  10 Washings with DMF | |
| 4a Acylation via symmetrical anhydride. Acylation time = 60 minutes. | (0.9 mmol). |
| 4b Acylation via hydroxybenzotriazole ester and DCC. Acylation time = 240 minutes. | (0.9 mmol) |
| 4c Acylation via p-nitrophenyl ester. Acylation time = 60 minutes. | (0.9 mmol). |
| 4d Acylation via pentachlorophenyl ester. Acylation time = 60 minutes. | (0.9 mmol). |
| 5  5 Washings with DMF. | |

TABLE 3

ORDER OF ADDITION OF THE AMINOACIDIC AND PEPTIDE DERIVATIVES USED IN THE SYNTHESIS AND PROCEDURE USED

| Derivative | Procedure |
| --- | --- |
| 1 Fmoc Val—Pro | 4b |
| 2 $N^\alpha$—Fmoc, $N^{im}$—Trt His | 4b |
| 3 Fmoc Pro | 4a |
| 4 $N^\alpha$—Fmoc, $N^\delta$—Boc Orn | 4a |
| 5 Fmoc Pro | 4a |
| 6 Fmoc Trp | 4a |
| 7 Fmoc Leu | 4a |
| 8 Fmoc Glp | 4d |

TABLE 4

| Decapeptide (mg/kg) | Duration of hypo-tensive effect | Pressure Difference | |
| --- | --- | --- | --- |
| | | Maximum | Minimum |
| II (0.3 mg/kg) (comparison) | 10 minutes | 15 mm$_{Hg}$ | 15 mm$_{Hg}$ |
| III (0.3 mg/kg) | >10 minutes | 20 mm$_{Hg}$ | 25 mm$_{Hg}$ |
| IV (0.2 mg/kg) | <10 minutes | 20 mm$_{Hg}$ | 25 mm$_{Hg}$ |
| V (0.2 mg/kg) | <10 minutes | 15 mm$_{Hg}$ | 15 mm$_{Hg}$ |

TABLE 5

| Decapeptides (mg/kg) | Duration of hypo-tensive effect (t) | Pressure Difference | |
| --- | --- | --- | --- |
| | | Maximum | Minimum |
| Decapeptide II (0.3 mg/kg) | 10 minutes | 15 mm$_{Hg}$ | 15 mm$_{Hg}$ |
| Decapeptide III (0.3 mg/kg) | 90 minutes | 15 mm$_{Hg}$ | 15 mm$_{Hg}$ |
| Decapeptide IV (0.2 mg/kg) | 45 minutes | 25 mm$_{Hg}$ | 30 mm$_{Hg}$ |
| Decapeptide V (0.2 mg/kg) | 30 minutes | 15 mm$_{Hg}$ | 30 mm$_{Hg}$ |

We claim:

1. A decapeptide having hypotensive action selected from the group consisting of:
   (a) Glp-Leu-Trp-Pro-Orn-Pro-Gln-Ile-Pro-Pro-OH;
   (b) Glp-Leu-Trp-Pro-Orn-Pro-His-Val-Pro-Pro-OH; and
   (c) Glp-Leu-Trp-Pro-Arg-Pro-His-Val-Pro-Pro-OH, wherein each amino acid of each compound has a L-configuration.

2. The decapeptide of claim 1 which is Glp-Leu-Trp-Pro-Orn-Pro-Gln-Ile-Pro-Pro-OH.

3. The decapeptide of claim 1 which is Glp-Leu-Trp-Pro-Orn-Pro-His-Val-Pro-Pro-OH.

4. The decapeptide of claim 1 which is Glp-Leu-Trp-Pro-Arg-Pro-His-Val-Pro-Pro-OH.

5. A pharmaceutical composition useful for the treatment of hypertension comprising a therapeutically effective amount of the decapeptide of claim 1 in combination with a pharmaceutically acceptable carrier.

6. The pharmaceutical composition of claim 5, wherein the decapeptide is Glp-Leu-Trp-Pro-Orn-Pro-Gln-Ile-Pro-Pro-OH.

7. The pharmaceutical composition of claim 5, wherein the decapeptide is Glp-Leu-Trp-Pro-Orn-Pro-His-Val-Pro-Pro-OH.

8. The pharmaceutical composition of claim 5, wherein the decapeptide is Glp-Leu-Trp-Pro-Arg-Pro-His-Val-Pro-Pro-OH.

9. A method of reducing blood pressure in a warm-blooded animal comprising administering to said warm-blooded animal a therapeutically effective amount of the composition of claim 5.

* * * * *

UNITED STATES PATENT AND TRADEMARK OFFICE
CERTIFICATE OF CORRECTION

PATENT NO. : 4,810,779
DATED : March 7, 1989
INVENTOR(S) : Valerio Caciagli, et al.

It is certified that error appears in the above-identified patent and that said Letters Patent is hereby corrected as shown below:

On the title page, change the name of the assignee to read as follows:

"Eniricerche S.p.A., Milan, Italy and Polifarma S.p.A., Rome Italy"--.

Signed and Sealed this

Twenty-sixth Day of December, 1989

Attest:

JEFFREY M. SAMUELS

*Attesting Officer*     *Acting Commissioner of Patents and Trademarks*